(12) United States Patent
Moscatello

(10) Patent No.: US 10,154,664 B2
(45) Date of Patent: Dec. 18, 2018

(54) SYSTEMS AND METHODS FOR THE DIGESTION OF ADIPOSE TISSUE SAMPLES OBTAINED FROM A CLIENT FOR CRYOPRESERVATION

(71) Applicant: David K Moscatello, Philadelphia, PA (US)

(72) Inventor: David K Moscatello, Philadelphia, PA (US)

( * ) Notice: Subject to any disclaimer, the term of this patent is extended or adjusted under 35 U.S.C. 154(b) by 109 days.

(21) Appl. No.: 13/646,647

(22) Filed: Oct. 5, 2012

(65) Prior Publication Data

US 2013/0122584 A1 May 16, 2013

Related U.S. Application Data

(60) Provisional application No. 61/544,103, filed on Oct. 6, 2011.

(51) Int. Cl.
| | | |
|---|---|---|
| *C12N 5/0775* | (2010.01) | |
| *A61K 35/35* | (2015.01) | |
| *A01N 1/02* | (2006.01) | |
| *A61K 35/28* | (2015.01) | |
| *B01L 3/00* | (2006.01) | |

(52) U.S. Cl.
CPC ............ *A01N 1/0263* (2013.01); *A61K 35/28* (2013.01); *A61K 35/35* (2013.01); *B01L 3/505* (2013.01); *B01L 3/5021* (2013.01)

(58) Field of Classification Search
None
See application file for complete search history.

(56) References Cited

U.S. PATENT DOCUMENTS

| | | |
|---|---|---|
| 5,372,945 A | 12/1994 | Alchas et al. |
| 5,716,616 A | 2/1998 | Prockop et al. |
| 6,673,606 B1 | 1/2004 | Tennekoon et al. |
| 7,390,484 B2 | 6/2008 | Fraser et al. |
| 7,514,075 B2 | 4/2009 | Hedrick et al. |
| 2003/0054331 A1* | 3/2003 | Fraser et al. ................ 435/2 |
| 2003/0161816 A1 | 8/2003 | Fraser et al. |
| 2004/0091936 A1 | 5/2004 | West |
| 2004/0106196 A1 | 6/2004 | Fraser et al. |
| 2005/0025755 A1 | 2/2005 | Hedrick et al. |
| 2007/0274965 A1* | 11/2007 | Mitchell, II ........ C12N 5/0647 424/93.7 |
| 2009/0181456 A1* | 7/2009 | Hedrick et al. .............. 435/366 |
| 2010/0136668 A1 | 6/2010 | Hedrick et al. |
| 2010/0233139 A1 | 9/2010 | Hedrick et al. |

OTHER PUBLICATIONS

Collagenase, Worthington Biochemical Corporation, Online Catalog, Accessed at http://www.worthington-biochem.com/cls/assay.html on Sep. 20, 2016.*
Soda R. and Tavassoli M. 1983. Adipocyte stem cell: a brief review, International Journal of Cell Cloning 1(2): 79-84. [Early use of "stem cell" in reference to ASC].

(Continued)

*Primary Examiner* — Kara D Johnson

(57) ABSTRACT

The present invention is directed to systems and methods of processing aspirated adipose tissue for the isolation of stromal vascular fraction derived stem cells.

10 Claims, 5 Drawing Sheets

(56) References Cited

OTHER PUBLICATIONS

Williams SK, McKenney S, Jarrell BE. 1995. Collagenase of selection and purification for adipose tissue digestion. Cell. Transplant. 4(3): 281-289, [Collagenese digestion of adipose tissue].
Strutt, B., Khalil, W., and Killinger, D. 1996. Growth and differentiation of human stromal cells in culture. In Methods in Molecular MedicineL Human Cell Culture Protocols, G.E. Jones, ed., Humana Press Inc., Totowa, NJ. pp. 41-51. [Isolation of ASC by Collagenase digestion; reduction of adipogenic differentiation when ASC are cultured with 10% FBS for more than a day].
Zuk, P., M Zhu. H. Mizuno, J. Huang, J.W. Futrell, A.J. Katz, and M.H. Hedrick. 2001. Multillineage cells from human adipose tissue: implications for cell-based therapies. Tissue Engineering. 7:211-228. [Used FBS in growth medium and all differentiation media].
Hauner, H., Skurk, T., and Wabitsch, M. 2001. Cultures of human adipose precursor cells. In Methods in Molecular Biology, vol. 155: Human Adipose Tissue Protocols, G. Alihaud, ed., Humana Press inc., Totowa, NJ. pp. 239-247.
Sengenes, Corelie, Lolmede, Karine, Zakaroff-Girard, Alexia, Busse, Rudi. Bouloumie, Anne. Preadipocytes in the human subcutaneous adipose tissue display distinct features from the adult mesenchymal and hematopoletic stem cells. Journal of Cellular Physiology 205(1):114-22, Oct. 2005.
Yoshimura, Kotaro, Shigeura, Tomokuni. Matsumoto, Daisuke, Sato, Takahiro, Takaki, Yasuyuki, Aiba-Kojima, Emiko. Sato, Katsujiro. Inoue, Keita Nagase, Takashi Koshima, Isao. Gonda, Koichi. Characterization of freshly isolated and cultured cells derived from the fatty and fluid portions of liposuction aspirates. Journal of Cellular Physiology 208(1): 64-76, 2006.

\* cited by examiner

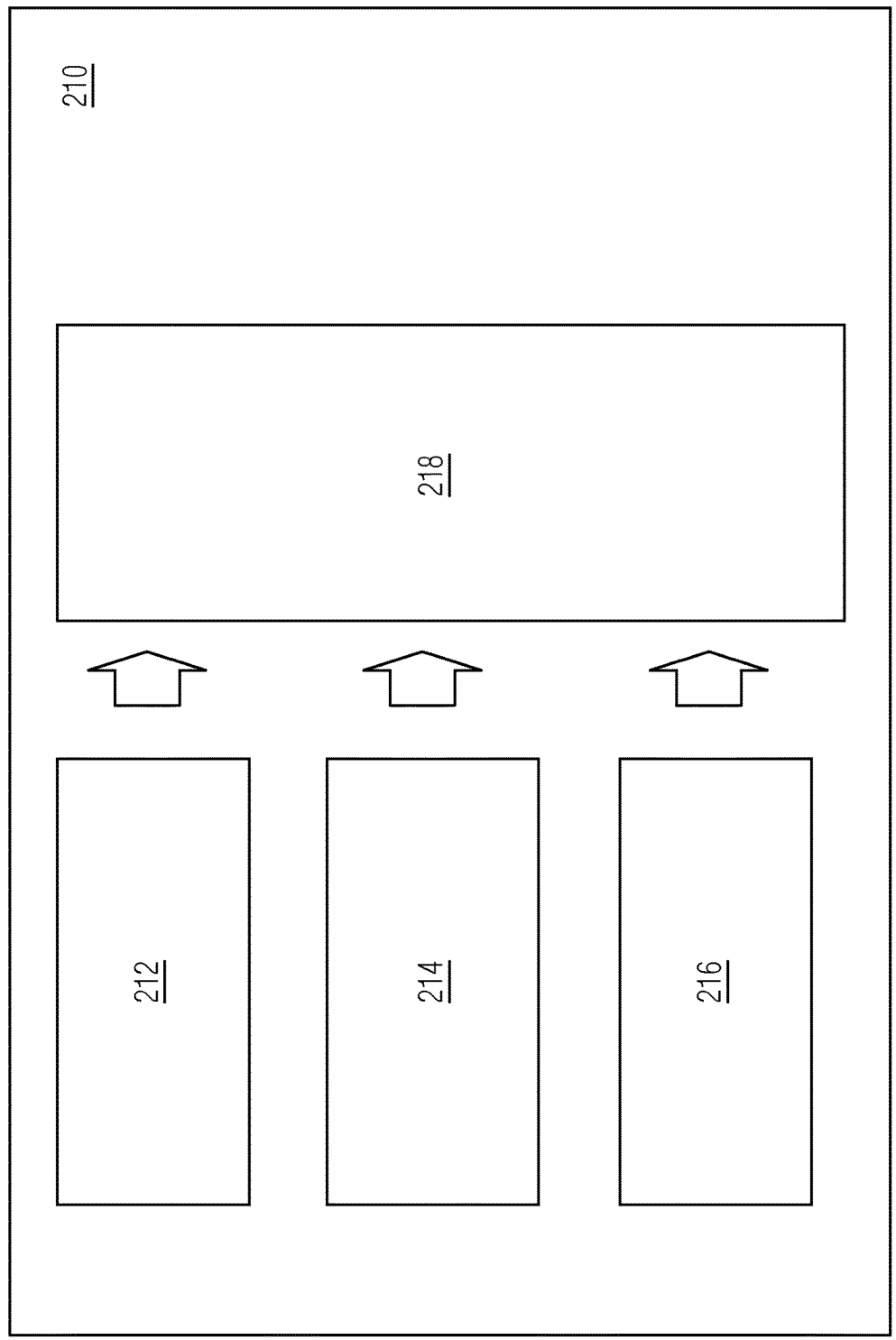

SYSTEMS AND METHODS FOR THE DIGESTION OF ADIPOSE TISSUE SAMPLES OBTAINED FROM A CLIENT FOR CRYOPRESERVATION

FIELD OF THE INVENTION

This invention relates to methods and systems for digestion of adipose tissue samples for the isolation of the stromal vascular fraction containing viable, uncontaminated stem cells, obtained from a client for cryopreservation, culture expansion or for immediate culture or cosmetic use.

BACKGROUND OF THE INVENTION

Conventional adipose tissue extraction methodologies and devices typically used within research formats to study, develop, and summarize theories and or conclusions, are unsuitable for clinical application. Because of the animal derived products and non-cGMP (current good manufacturing practices) materials used in laboratory techniques during the handling and processing, use of the final products would be impermissible for human application. Advancements in tissue handling, manipulation, and processing techniques are being developed for the immediate clinical application of the processed adipose tissue materials.

In recent years, the discovery of adipose-derived stem cells in the stromal vascular fraction (SVF) of adipose tissue, specifically mesenchymal stem cells, have led to advances in tissue re-growth and differentiation. The SVF is that portion of adipose tissue other than the mature adipocytes, which can be separated after enzymatic digestion of the tissue to release individual cells from the extracellular matrix, followed by centrifugation. This fraction contains monocytes (white blood cells), erythrocytes (red blood cells), mesenchymal stem cells, committed preadipocytes, microvascular (capillary) endothelial cells, and endothelial progenitor cells. A particular future use of adipose-derived stem cells—the stromal vascular fraction, more specific to mesenchymal stem cells, could be the enhancement of the body's natural beating capabilities.

Concerns regarding clinical applications of adipose tissue derived stem cells in the medical community are based on the possibility of pathogen and xenogenic pathogen contamination due in part to fetal bovine serum or animal sera used in culture media of cells. Because of the research grade techniques used during the handling and processing of tissue samples, use of the final products would be unsuitable for human application (Preadipocytes in the human subcutaneous adipose tissue display distinct features from the adult mesenchymal and hematopoietic stem cells. Journal of Cellular Physiology 205(1):114-22, 2005 October and Characterization of freshly isolated and cultured cells derived from the fatty and fluid portions of liposuction aspirates. Journal of Cellular Physiology 202(1): 64-76, 2006).

There is an immediate and long-felt need for methods and systems for the utilization of human tissue to be suitable for clinical application. The present invention satisfies these needs with respect to adipose tissue and adipose tissue-derived stem cells.

BRIEF SUMMARY OF THE INVENTION

In a first embodiment, the invention is directed to a method of isolation of stromal vascular derived stem cells which is initiated by supplying an shipment package including a defined client sample container and thereafter, inspecting shipment package components for (i) integrity of a client sample container containing an adipose tissue sample and (ii) completed recording information, contained therein. In a preferred embodiment, the shipment package components are introduced to a processing module of a database via a log-in port by scanning a barcode on the client sample container in the completed recording information. The method continues by removing collection medium in the client sample container and washing the adipose tissue sample. Preferably, oil dispersed from the adipose tissue sample is substantially removed and a digestion solution is prepared. The digestion solution is injected into the adipose tissue sample to form a digestion mixture within the client sample container, and incubating the digestion mixture. The incubated digestion mixture is incubated and thereafter centrifuged. Withdrawing a stromal vascular fraction phase of the centrifuged digestion mixture and centrifuging a suspension of the filtered digestion mixture isolates a first stromal vascular pellet. Thereafter, the supernatant of the centrifuged suspension is removed and the first stromal vascular pellet is re-suspend by trituration in red blood cell lysis buffer forming a cell suspension. The cell suspension is centrifuged to form a second pellet. The cell suspension of the centrifuged solution is removed, and thereafter, the second pellet is re-suspending by trituration adding salt solution forming a second suspension. The second cell suspension is centrifuged to form a third pellet, retaining the supernatant from the third pellet for a secondary sterility test sample.

In another embodiment the invention is directed to a system for isolation of stromal vascular derived stem cells including a shipment package, a database, at least one sterility test system, a digestion solution, at least one separation container, viability testing, and a storage facility.

BRIEF DESCRIPTION OF THE DRAWINGS

FIG. 3 illustrates the system;

DETAILED DESCRIPTION OF THE INVENTION

Figure 1:
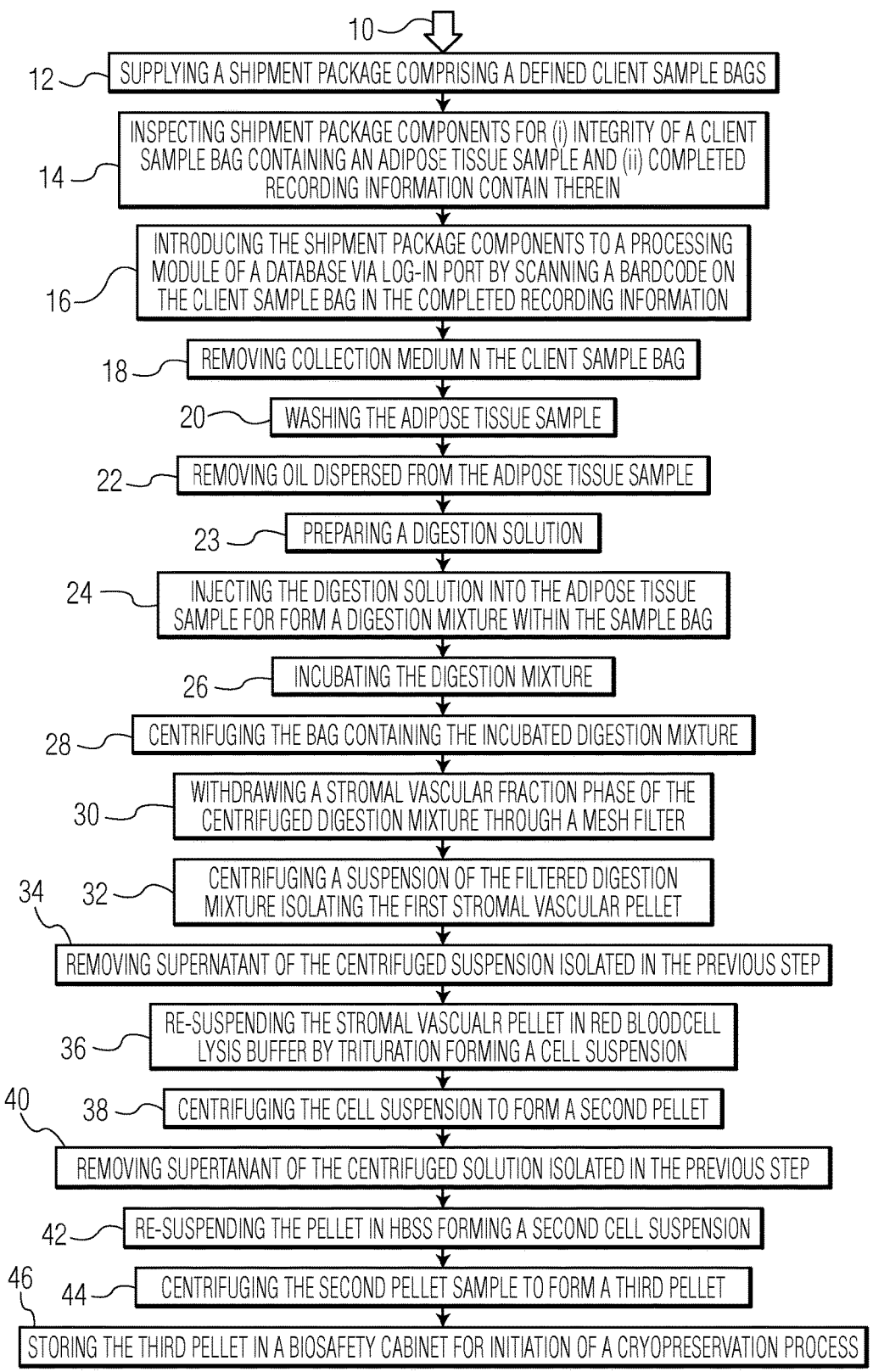
FIG. 1 is a flowchart of the method of the present invention.

Certain terminology is used herein for convenience only and is not to be taken as a limitation on the present invention. The terminology includes the words specifically mentioned, derivatives thereof and words of similar import. The embodiments discussed herein are not intended to be exhaustive or to limit the invention to the precise form disclosed. These embodiments are chosen and described to best explain the principle of the invention and its application and practical use and to enable others skilled in the art to best utilize the invention.

In a first embodiment, the invention is directed to a method of processing aspirated adipose tissue for the isolation of stromal vascular fraction (SVF) derived stem cells 10. The method is initiated by supplying a shipment package including a defined client sample container 12. The shipment package can include various components in addition to the defined container with client information for extraction of the adipose tissue sample by a physician. Thereafter inspecting the shipment package components for (i) integrity of as client sample container containing an adipose tissue sample and (ii) completed recording information, contained therein 14 is performed at a designated laboratory site or other designated facility site.

The design of the client sample container is an important feature for various embodiments of the invention of the present application to obtain the desired resultant product(s) in a financially effective and labor efficient manner. Therefore, the following defines key important features of the container design and the importance of each feature. One skilled in the art would recognize the following description is not intended to be limiting but to encompass the required features.

The client sample containers should be made of material such as ethyl vial acetate and/or polyethylene, or fluoro-ethylene propylene, or combination thereof, which does not release or leach any potentially toxic substance into stored cells. Fluoro-ethylene propylene (FEP) has the potential advantage of being gas permeable, so oxygen can diffuse in and carbon dioxide out, which may improve cell viability during storage and transport. Further, the containers must be FDA-approved for use in storage of blood, cells or blood-derived products to allow for clinical applications.

The client sample containers should be sterile and approximately 100 ml to 200 ml in volume so as to contain an adequate adipose tissue (AT) sample and requisite medium which can maintain the viability of the adipose tissue for processing and use (as discussed herein). The containers must have at least three (3) ports; one for adding the collection medium, one for adding the aspirated adipose tissue, and one for removing the medium, adding the washes and digestion enzyme, and removing the SVF fraction. A preferred configuration of the client sample container would have five (5) ports, three on top, one in the center of a tapered bottom, and one to a side of the bottom. At least one filter is included within the container for separation.

All ports except one should be "female" ports, one port can be for a spike, (e.g. a large-bore, plastic "needle" meant to be inserted once into a port and subsequently kept in place located on a lower end of the container so as to allow gravity for draining contents as appreciated by those skilled in the art. For example, there is a spike on a 40 micron mesh filter used to recover the SVF from the container alter digestion. The spike is nearly the diameter of the port tubing and fits in tightly. Since this is the last time the container is used, the integrity of the container after this step is immaterial. All of the ports must have caps to ensure the exclusion of contamination. In a preferred embodiment, the ports used to introduce the collection medium and the adipose tissue would have needle-free access ports for the direct connection for the Luer-lock syringes.

The tubing on the ports should be no more than 6 inches in length. Long tubing would be a waste of space and material and could cause loss of sample; e.g., fat could get clogged or adhere in the tube. The ports include tithing connecting the port opening with the inside of the container.

Figure 2:
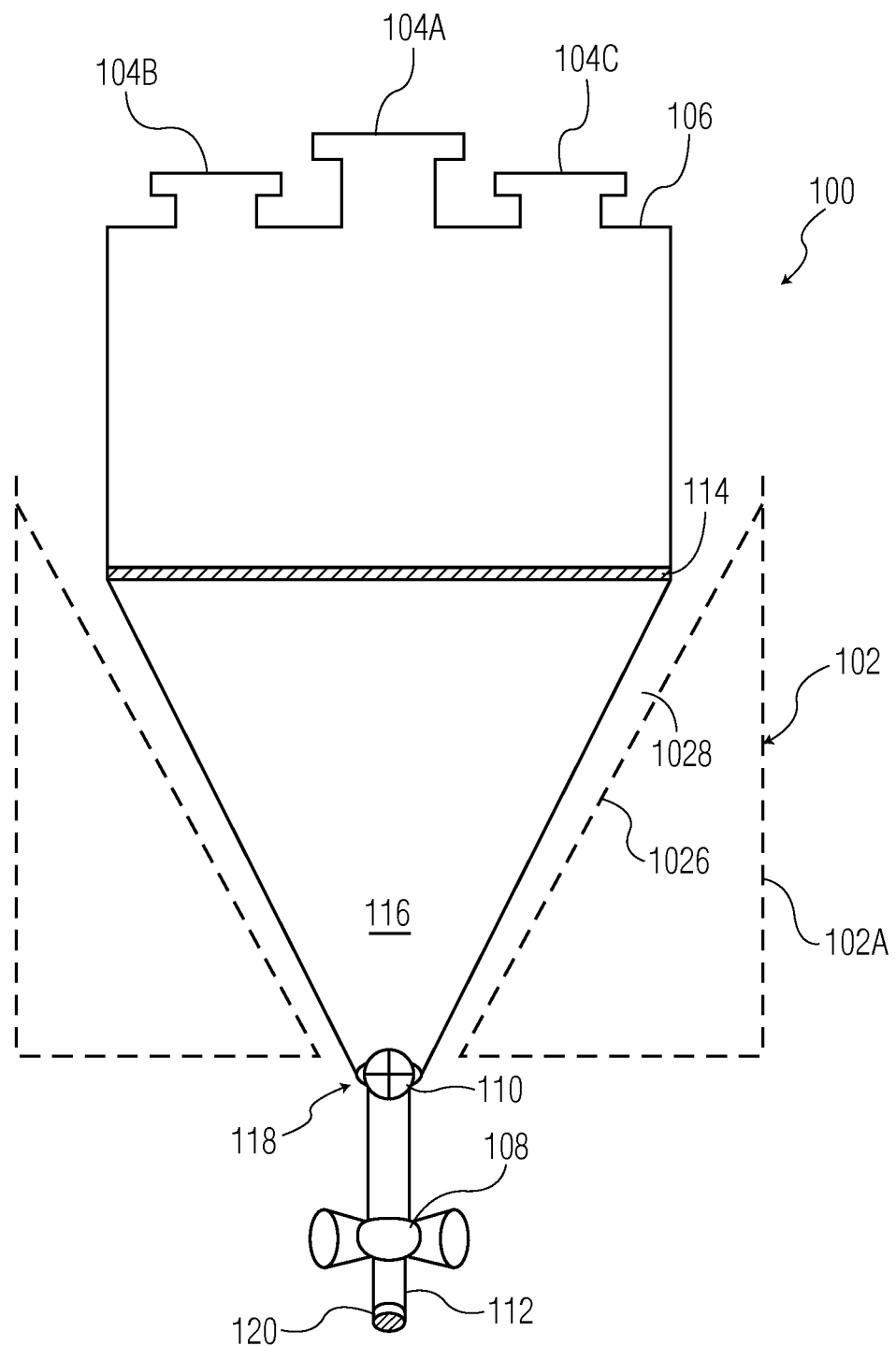
FIG. 2 is a preferred embodiment of the container of the present invention.

Referring to FIG. 2, a preferred example of the container 100 is illustrated with a complementary centrifuge insert 102 (shown in phantom). In the preferred example, the container 100 includes a Physician port 104A, a medium entrance port 104B, and an oil removing port 104C on a top side 106 and a 3-way port 108 on a bottom side 110. The Physician port 104A, a medium entrance port 104B, and an oil removing port 104C are color coded to avoid contamination. Moreover, the Physician port 104A may include a pierced septum for direct connection to a syringe. In a preferred embodiment, the 3-way port 108 includes a spike port 112 positioned perpendicular to the bottom side 110, a sufficient distance from the 3-way port 108 and final filter 110 to preclude interfering with the function of either component. One of the ports on the 3-way port may be a needle septum port for collection of the microbial sterility test sample.

The container 100 includes a filter 114 extending the width of the container 100, wherein the filter 114 initiates a tapered section 116 of the container 100. The tapered section terminates at the 3-way port 108. A second filter 118 traverses the bottom side 110 distal to a terminus end 120 of the spike port 112. The filter is approximately 100 micrometer nylon mesh, preferably 100 to 200 micrometer, and the second filter is approximately a 40 micrometer nylon mesh, preferable 40 to 100 micrometer nylon mesh. The 100 micrometer mesh filter will allow individual cells of the SVF to pass through, but will exclude large, mature adipocytes and clumps of smaller cells still held together by extracellular matrix material, and will also reduce the potential or clogging the smaller mesh filter below. The 40 micrometer mesh filter will exclude most immature adipocytes and smaller clumps of cells, but will allow isolated SVF cells such as adipose stromal cells and endothelial progenitor cells to pass.

Figure 2A:
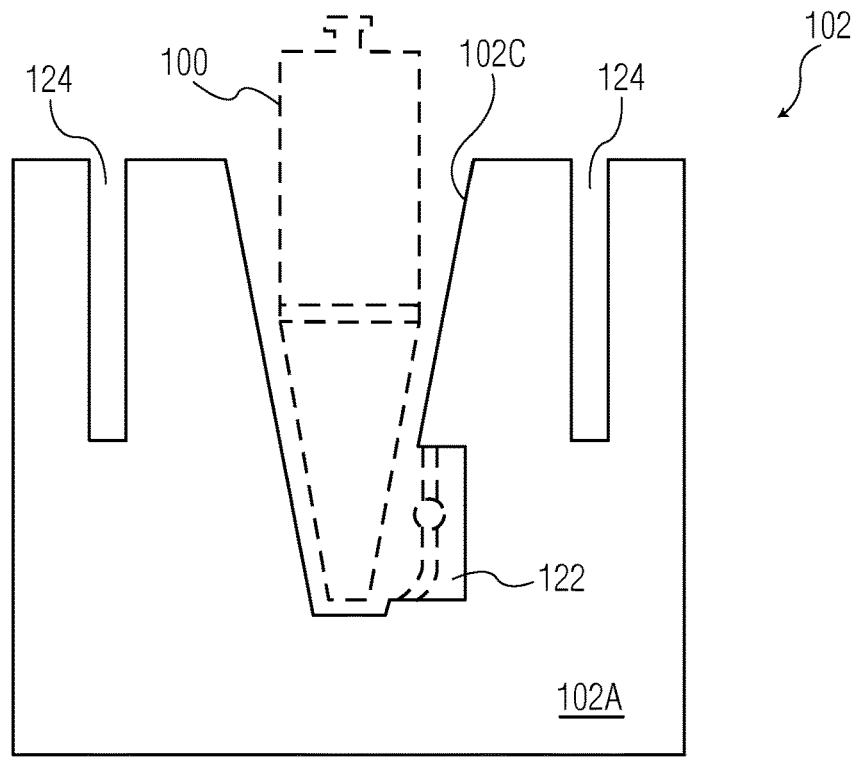
FIG. 2A is a side view of a complimentary centrifuge insert illustrating the container in phantom.
Figure 2B:
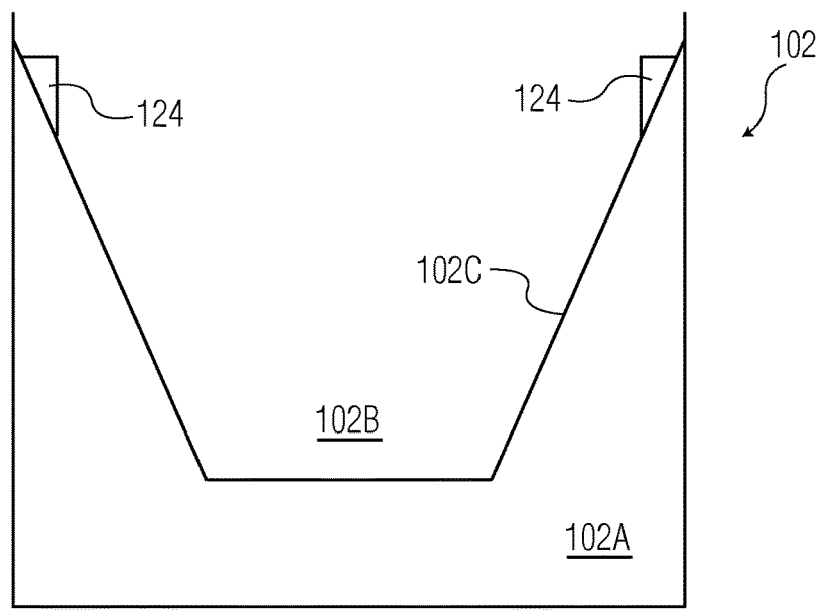
FIG. 2B is a plan view of the complimentary centrifuge insert for the container.

Referring to FIGS. 2, 2A and 2B, the complementary centrifuge insert 102 has an exterior surface 102A which fits into a standard bucket type centrifuge such as Beckman GS-6R with a GH 3.8 swinging bucket rotor. A central insert section 102B for placement of the container 100 defines an interior portion 102C. The interior surface 102C includes pocket inserts 122 which are positioned to accept the 3-way port 108 at the bottom side 110 of the container 100 (shown in phantom) in a folded position as best illustrated in FIGS. 2A and 2B. In the folded position, the dimensions of the container 100 allow the "fold" to act a locking mechanism to eliminate leakage during centrifuging the sample (as discussed herein). The container could have thicker areas or ridges immediately above and below the site of the fold to enhance the seal when the container folded, in a fashion similar to a zipper-top container. Alternatively, the container could be tightly sealed after folding by attaching a clip similar to as binder clip by sliding or clamping his could also lock the container into position more securely into the centrifuge bucket insert. Thus, centrifuging forces the sample through the filter 114 but the position "fold" eliminates leakage. Referring again to FIG. 2A, the insert 102 includes weight adjustment pockets equally spaced on either side of the central insert section 102B.

Again referring to FIG. 1 illustrating the method, after filling with collection medium, the client sample containers are sealed in outer containers before shipping. The outer container is to protect the inner container, particularly ports which have been accessed, from contamination. The outer containers also serve to prevent leakage and contamination of the shipping container incase the integrity of the inner container is compromised. Outer containers do not have to be sterile, and don't have to be of the same material as the inner containers, because the cells will not come in contact with the outer containers. The outer containers must be sealable, and can be commercially obtained separately.

Inspecting the shipment package 14 includes ensuring that (a) the collection container is not past a defined expiration date, (b) the client sample was collected within the past 48 hours, and (c) the recording information is accurate. If the conditions set in any of a, b, or c are not met, then the sample is not acceptable and must be discarded as biohazard waste. This discard will be recorded for organization and "tracking" of the sample.

Most commonly, the shipment package includes a barcoded, medium-filled client sample container in an outer container as discussed herein), a sterile, 60 cc syringe, a patient-specific bar-coded shipping container approved for biohazardous materials containing an absorbent sheet, a Tyvek® outer container, sufficient bubble-wrap to stabilize the contents, and foam insulation in an outer corrugated cardboard box (the latter items commercially available from Saf-T-Pak®). The appropriate needles cannula and other medical supplies are generally accessible equipment which will be supplied by the physician, but may be included as part of the shipment.

The method continues by introducing the shipment package components to a processing module of a database via a log-in port by scanning a barcode on the client sample container in the completed recording information 16. The database will be custom-designed to have the ability to comply with the requirements of the American Association of Blood Banks (AABB) standard 6.3 and 21 CFR § 820.30 (FDA Guidance, Jan. 11, 2002, "General Principles of Software Validation) using, for example, it commercially available program such as Microsoft's Access program. The database will include but is not limited to, the information obtained from the shipment package to coordinate the client sample with the client, such as the in formation included in the patient-specific bar-coded shipping container. This information will also be included in a standardized form. The database may be organized in modules similar to the organization in the standardized form, will be searchable, and will be programmed to produce all the various forms associated with this process.

At the establishment of an acceptable client, sample, one vial each of collagenase, neutral protease, and DNase I is removed from a freezer and thawed in a biosafety cabinet for use in a digestion solution. Alternatively, a pre-defined mixture of collagenase and neutral protease may be used, e.g. Roche Liberase®, which contains both collagenase I and collagenase II, plus thermolysin, a neutral protease. Thawing at room temperature, or at refrigerator temperatures (about 2 to 8 degrees centigrade, and without assistance supports in the protection of the integrity and viability of these solutions.

The sample(s) meeting the requirements set forth above, are removed from the outer container and gently agitated in the client sample container manually to re-suspend the fat and any sediment in the medium, and further, to ensure that the sterility test samples will be representative of the contents. The sample container is wiped, most commonly with alcohol to ensure it is not contaminated. Most commonly spray bottles are used with filter-sterilized 70% ethanol or isopropanol The diem sample container is "hung" and allowed to stand undisturbed for approximately live (5) minutes, preferably 5 to 15 minutes, to note the presence of visible blood and estimate the amount of oil from lysed fat as a fraction of the total adipose tissue present in the client sample. This observation is recorded in a defined manner usually on it predesigned form. Observations such as the amount of oil present will be entered into a standardized form, and thus become part of the database. The completed forms can be minted for backup records. For coordination and ease, the forms will all be fill-able online, h is appreciated that upon log-in into the system, they will be able to choose the form(s) needed for whichever process they are performing in collection, storage and distribution of the client sample, in this case, the digestion processing. The bar codes on the containers will be scanned, and the information in the barcode will be imported into the form from the database.

Sterility of the AT sample within the client sample container is tested to ensure the quality. The test most commonly includes disinfecting the bottom port prior to removal of a defined amount the collection medium 18. In the event the antibiotic agents are included in the collection medium, the collection of a sterility test sample at this stage may be omitted, and replaced with a test of the saline solution wash instead. The removal via a bottom port allows extraction by gravitational force thus eliminating any need for a "pump" etc. Sterility and microbial testing is performed by standard commercial systems such as BacT/Alert or similar testing. Specific testing procedures are performed in order to comply with and receive required AABB or other professional organization certification and adhere to specific current and future FDA rules as applicable.

Sterility samples are kept at room temperature until sent to the testing laboratory. Recognizing there are only a limited number of ports on the container, the same port is used to remove the collection medium from client sample container that was used to obtain the sterility sample. The medium is then discarded. The same port is used because the outer part of the port could be contaminated. Since all the processing will be done in a biosafety cabinet, the chances of contamination during the processing in the laboratory are less than in the physicians' procedure room.

The AT sample is washed 20 by disinfecting one of the top ports, most commonly by wiping with 70% or sterile alcohol with a swab, and adding a defined amount of salt solution. The defined amount is at least equal to the volume of adipose tissue sample to wash it effectively. The salt solution, e. Hank's Balanced Salt Solution (HBSS), is added by using a 60 cc syringe with an 18 gauge needle, or alternatively, a split septum needle-free port such as the BE) Q-Syte™ Luer access port may be used to add and remove solutions.

One skilled in the art would recognize ports come in several different types, most must be traversed using either a needle or a spike (basically, a fat plastic needle). An 18 gauge needle is used commonly as an efficient removable tool. It is understood, the lower the gauge number, the larger the needle diameter. While a smaller needle (such as 27 gauge) makes a smaller hole, and thus damages the septum less, it is harder to inject or remove the large volumes of medium needed in the digestion process. All ports for needles have Luer® fittings, as do all the syringes which are used, which are identical regardless of needle size.

The client sample container is gently agitated and allowed to stand undisturbed for a defined time period most commonly about five minutes, or a range of five to fifteen minutes. Using the same port that was used to obtain the sterility sample, the wash is removed and discarded. The container is allowed to hang undisturbed again until fat is observed floating in a single layer at the top of the container, oil (if present) on top of the fat. Alternatively, the container may be briefly centrifuged at as low relative centrifugal force, for example, 800 revolutions per minute for 3 minutes, in order to separate the phases.

Oil dispersed from the adipose tissue sample is substantially removed 22. If there is significant (> about 5 mL) oil on the top of the AT sample; as much of the oil as possible should be removed without disturbing the AT sample by maneuvering the container so that the oil is positioned by one port; using a syringe and needle complementary to the port. If blood or oil is still visible after the first wash, the AT sample can be washed again with the salt solution as described above, allowing the sample to separate before removing wash buffer, the HBSS wash defined herein.

A digestion solution is prepared 23 as discussed herein and is injected into the client sample container having the adipose tissue sample to form a digestion mixture within the client sample container. The outside of the vials of collagenase, neutral protease, and DNase or combination product thereof, for the digestion solution (thawed as previously discussed for use herein), are wiped to ensure sterility, most commonly with an alcohol swab.

Using sterile, 2 ml pipets transfer the solutions to a 50 ml centrifuge tube containing 48 ml HBSS pre-warmed to 37° Celsius. The tube is capped and mixed by gentle agitation of the tube. Alternatively, this can be done using vials with a septum for needle access, and syringes with attached needles, to maintain a closed system (not directly exposed to air) to further reduce the risk of microbial contamination. The basis of this dilution ratio is the concentration and enzymatic activity of the enzyme stock solutions, which are based on (i.) product protocols (ii.) experience, and (iii.) what is known in the art. In regard to "what is known in the art", most workers routinely make enzyme solutions as a weight/volume percentage, or milligrams per milliliter, for example, 0.1 percent collagenase, or 1 milligram per milliliter, is widely used for digestion of adipose tissue (Growth and differentiation of human adipose stromal cells in culture. In *Methods in Molecular Medicine: Human Cell Culture Protocols,* 1996, 41-51. An advantage of the protocols developed in the instant application is to base the dilution on the amount of enzyme activity, rather than simply weight/volume ratios, since the activity of different enzyme lots can vary drastically. For example, 1 mg of lot "A" might have one unit of activity, whereas 1 mg of lot "B" could have only 0.7 unit of activity. Therefore, a 1 mg/mL solution of lot "B" enzyme would only have 70% of the activity of a 1 mg/mL solution of Lot "A" enzyme, resulting in less efficient digestion. The method of the instant application eliminates this variable by basing the enzyme dilution on the specific activity rather than the mass, making the process more reproducible. This is critical for a commercial process.

The digestion solution is injected 24 into the washed AT sample using one of the top ports of the container. The digestion mixture is incubated 26 at 37 degrees Celsius for 45 minutes while being agitated on a rocking platform at about 24 rocks per minute, or in a range of 24 to 48 rocks per minute. At the end of the digestion, the adipose tissue is converted from a suspension of tissue fragments up to 4 millimeters in size into a much smoother suspension in which most tissue fragments are less than 1 millimeter in diameter, as most of the adipose tissue is dissociated into isolated mature adipocytes and stromal-vascular fraction cells, although some whitish, connective tissue may remain intact. Thereafter, the solution is centrifuged at a low speed to separate the mature adipocytes from the rest of the digestion mixture 28.

The stromal vascular fraction phase of the centrifuged digestion mixture is withdrawn 30 through a sterile, 40 micrometer mesh filter. The centrifugation of the digestion mixture in the container serves to separate the SVF from the adipocytes and undigested adipose tissue. More specifically, the first low-speed centrifugation, while the digestion mixture is still in the container, separates the oil and fat from the stromal-vascular fraction. However, the geometry and composition of the proposed container does not allow for a concentrated pellet since the stromal-vascular fraction pellet is very small, typically less than 0.1 milliliters, and the container narrows gradually from the full width about midway down the container. The stromal vascular fraction thus spreads out over a fairly large area near the bottom. Removing this SVF from the container to a centrifuge tube and re-centrifuging allows formation of a "tight" pellet at the bottom of the tube (as discussed herein), so that greater than 95 percent, and as much as 99 percent, of the enzyme solution can be removed. One skilled in the art would appreciate the container plastic (discussed previously herein) permits greater adhesion than the rigid polypropylene of which most disposable centrifuge tubes are made, and significant amounts of debris are released from the adipose tissue during digestion, so some of the SVF material is able to adhere to the inside of the container hear the bottom The suspension of the filtered digestion mixture is centrifuged in two 50 mL tubes upon removal from the container, isolating the first stromal vascular pellet 32. The supernatant of the centrifuged, filtered suspension isolated is removed 34. The stromal vascular "tight" first pellet is re-suspended 36 by trituration in a red blood cell lysis buffer, eliminating red blood cells, as well as removing residual enzymes and debris, forming a cell suspension which is centrifuged to form a second pellet 38. This serves as another wash, and removes hemoglobin released from lysed red blood, cells. The supernatant of the centrifuged cell suspension is removed 40.

The second pellet is re-suspended by titration adding HBSS forming a "second cell suspension" 42. This second cell suspension can be counted and analyzed for viability using; 1) stains specific for live and/or dead cells and a hemacytometer with a microscope, or 2) a commercially available automated cell analyzer. In a preferred method of counting and analyzing the of the second cell suspension, a small aliquot (20 microliters) of the second cell suspension is mixed with an equal volume of a mixture of acridine orange and propidium iodide stains and counted using the Nexcelom Cellometer Vision instrument (Nexcelom Biosciences). The second cell suspension is centrifuged 44 to form a third pellet which is stored in a biosafety cabinet for initiation of a cryopreservation process 46. Furthermore, the supernatant of the third pellet serves as a secondary sterility test sample which may reveal the elimination of contaminants that may have been present in the initial sample, and ensure that no contamination was introduce during the processing in the laboratory.

The "third pellet" defines a stem cell pellet product, e.g. a washed SVF pellet, produced by the method, wherein the stem cell pellet includes a mixture of cells of pre-adipocytes, adipose-derived mesenchymal stem cells, microvascular endothelial cells, endothelial progenitor cells, monocytes, and small numbers of vascular smooth muscle cells. The mixture must contain no mature adipocytes, and at least 1% of the nucleated cells in the mixture must be adipose-derived mesenchymal stem cells. The mixture or "stem cell pellet product" or "washed SVF pellet" must exhibit a combined viability by acridine orange/propidium iodide or trypan blue dye-exclusion assay of no less than 35%. Further, the adipose-derived mesenchymal stem cells contained therein must be capable of proliferation when placed in contact with a suitable culture medium under appropriate environmental conditions known to those skilled in the art of cell culture.

In another embodiment, the invention is directed to a system for isolation of stromal vascular derived stem cells. Referring to FIG. 3, the system 210 includes a shipment package 242, a processing system 214, at least one storage facility 216 and a database 218. The database 218 stores information obtained from the shipment package 212, processing system 214, and at least one storage facility 216.

Figure 4:
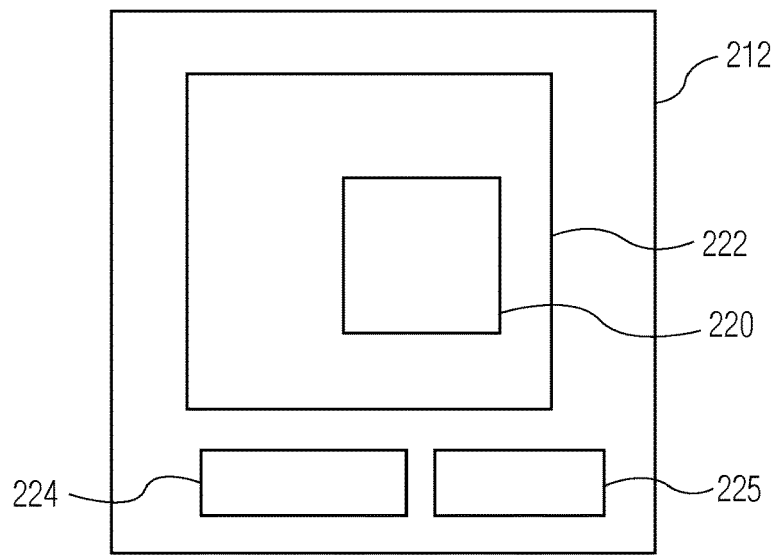
FIG. 4; is a plan view of the shipment package of the system.

Referring to FIG. 4, the shipment package 212 includes a bar coded client sample container 220, a sheet of absorbent material that must be capable of absorbing all of the fluid in the sample (not shown), and should be Department of Transportation/International Air Transport Association] approved for shipping biological or medical samples. A second container 222, most commonly a zipper-top plastic container to contain the client sample container and the sheet of absorbent material, and a form of recording information 224 are also included. The third container 225 contains the bar coded client sample container 220 for the return shipment to the processing laboratory and is most commonly, a commercially available Saf-T-Pak® container including, a plastic container and may include a Tyvek® container.

The form of recording information 224 works in tandem with the database 218. The database 218 includes an encoded program to organize and store information regarding the sample and recording information and is customized to the specific requirements for the coordination of samples to the client. The database 218 will include all data, not just for storage, identification and distribution, and further information obtained from the second bar coded container 222. In addition, the database 218 will include information regarding preparation of all reagents.

Figure 5:
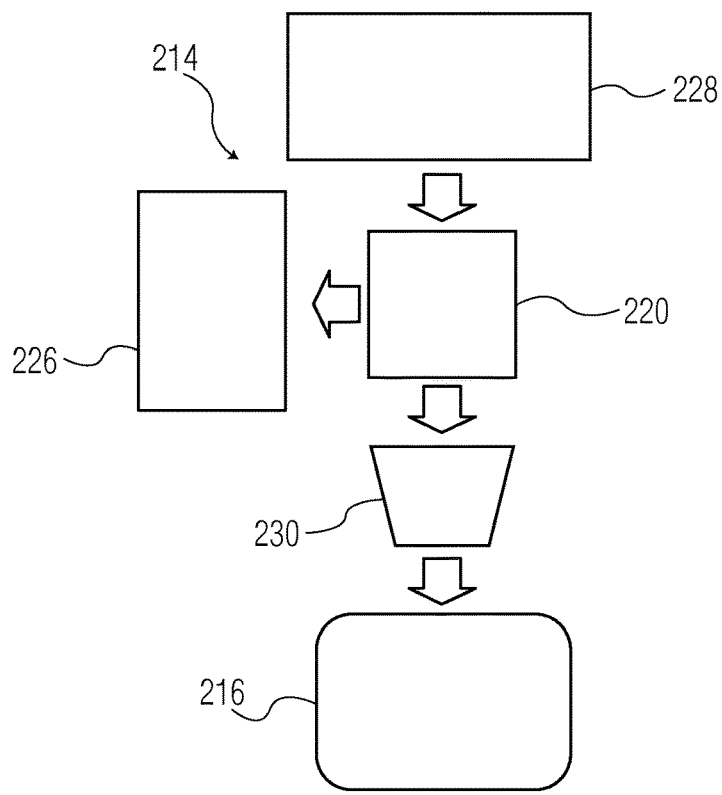
FIG. 5 illustrates the sample container of the shipment package and the digestion solution, sterility test program, at least one separation container and storage container of the system.

Referring to FIG. 5, the processing system 214 includes at least one sterility test system 226, a digestion solution 228, and at least one separation container 230. Each component of the processing system 214 has been described here in regard to die method embodiment herein. As best illustrated in FIG. 5, the processing system 214 components work in a coordinated manner with other elements of the system 210.

The sterility test system 226 includes a combination of one BacT/Alert—iAST sample bottle and one BacT/Alert—iNST incubated at designated temperature (s) in the Bio-Mérieux BacT/Alert system. It is recognized that other sterility tests could be used including fluid thioglycollate medium, soybean-casein digest medium, and blood agar plates incubated at the appropriate temperature(s). All the test bottles in the lab will be inoculated and either tested in-house on the BioMérieux BacT/Alert system or sent out for such testing. All sterility test cultures must be incubated at 30°-37° C. for fourteen (14) days, except for soybean-casein digest medium which may be incubated at 20-25° C., for a minimum of 14 days and inspected on days 3, 4, or 5, days 7 or 8, and day 14 for turbidity (broths) or colony formation (blood agar plates). Results of each observation will be recorded, most commonly pursuant to 21 CFR § 610.12.

The present invention will now be described based on the following examples.

Example 1

| Step | Action |
|---|---|
| 1 | Upon receipt, inspect the shipment for (a) the client sample container(s) and (b) the completed form. Ensure that the integrity of the sample container(s) is intact. If the sample container is not bar-coded, or if there is any evidence of leakage from the container(s), the sample is not acceptable and must be forwarded to quality management and the Laboratory supervisor notified. |
| 2 | Print labels matching the barcode on the sample and place on the (2) 50 mL tubes, two (2) 15 mL tubes, and one (1) 12 mL tube required. Print four additional labels for the batch record and the three CellSeal vials. At least two of the labels must be in a wrap-around format and one long format. |
| 3 | Remove one vial of collagenase MNP-S from the −80° C. freezer and thaw in biosafety cabinet (BSC), and place one vial of DNase I from the −20° C. freezer in the BSC. |
| 4 | Remove the sample(s) meeting the requirements set forth in 1 and 2 above, from the overwrap and gently rock the container manually three times. Weigh the container on the top-loading scale and record the weight. Wipe the sample container with 70% alcohol, hang the container from the IV bar in the biosafety cabinet, and allow to stand undisturbed for ten (10) minutes. Note the presence of visible blood and estimate the amount of oil from lysed fat as a fraction of the total adipose tissue (AT) present in the sample, and record. |
| 5 | Snap the cap off the needle access port, wipe the port with a 70% alcohol swab and remove 20 mL of the collection medium using a 20 cc syringe with an 18 gauge needle. Inoculate 10 mL into one BacT/Alert-iAST sample bottle and 10 mL into one BacT/Alert-iNST for physician sample sterility testing. These are kept at room temperature (20°-25° C.) until sent to the testing laboratory. |
| 6 | Using the Q-Syte port, remove the remaining collection medium using an 18 gauge needle on a 60 cc syringe and discard. Re-weigh the container, record the weight, wipe with 70% alcohol, and return to the BSC. Wipe the Q-Syte port with a 70% alcohol swab and add 50 mL of Hank's Balanced Salt Solution (HBSS) using a 60 cc syringe. Gently rock the container manually three times by hand and centrifuge at 800 rpm for three (3) minutes. |
| 7 | Return the container to the BSC and hang on the IV bar. Wipe the Q-Syte port with a 70% alcohol swab, attach a 60 cc syringe and remove and discard the wash solution. Re-weigh the container, record the weight, wipe with 70% alcohol, and return to the BSC. |
| 8 | Wipe the outside of the vials of collagenase and DNase I with a 70% alcohol swab. Using a sterile, 2 ml pipet, transfer the collagenase solution to a 50 ml centrifuge tube containing 49 ml HBSS pre-warmed to 37° C., rinse the vial with 2 mL of the solution and add the rinse to the tube. Then add 0.2 mL (200 μL) of the DNase I stock to the tube using a micropipettor, cap the tube and mix by gently swirling the tube. This is the digestion solution. |

| Step | Action |
|---|---|
| 9 | Prop the container against the tube rack with the ports pointing up above the rack. Wipe the Q-Syte needle-free access port with a 70% alcohol swab. Remove the plunger from a sterile 60 cc syringe and attach the syringe to the Q-Syte port. Pour the digestion solution into the syringe, and then open the clamp on the container port to allow all of the solution to enter the container. Close the clamp on the container and remove the syringe. |
| 10 | Fold the container over at the bottom where the ports enter the container and secure with a rubber band. Place the digestion container on the rocker platform in the 37° C. incubator and incubate for 45 minutes at 24 rocks per minute. |
| 11 | During the digestion period, the technician may log-in and perform steps 1-10 of a second AT sample if necessary to complete processing of all samples on the date received. |
| 12 | After digestion is completed, remove the container from the incubator back to the Biosafety cabinet and add another 50 mL of HBSS via the Q-Syte port using a sterile 60 cc syringe. Rock the container manually 3 times and place in the blood container cup in the centrifuge. Ensure that there are no tight creases in the container, that the container is stably in position, and that the central, bottom port is centered in the bottom of the bucket, and then put on the bucket cover. Ensure that the rotor is balanced by placing the bucket on the beam balance against the opposite bucket containing a sham sample container, and adjusting the mass of the balance bucket by adding or removing water from the sham container or a centrifuge tube in the bucket as needed. Centrifuge at 800 rpm for 3 minutes. |
| 13 | Remove the digestion container from the centrifuge bucket, taking care not to disturb the separated phases, and hang in the biosafety cabinet. Remove the cap from the third, unused male luer port and attach a sterile 40 μm mesh filter to the port. Gently massage the lower portion of the container to release any cells diffusely pelleted on the container. |
| 14 | Loosen the caps on the two labeled 50 mL tubes, remove the cap from the spike at the end of the filter, and drain the bottom phase containing the stromal-vascular fraction (SVF) through the filter into two (2) 50 mL centrifuge tubes. |
| 15 | Ensure that the tubes balance, and then place the tubes in opposite 50 ml tube buckets. Centrifuge at 1,200 rpm for 10 minutes. |
| 16 | Remove the tube(s) from the centrifuge bucket, taking care not to disturb the SVF pellet, and place in the biosafety cabinet. Using an aspirating pipet attached to the vacuum set-up, remove as much of the supernatants as possible (all but ≤1 ml). Re-cap the tubes, flick the bottom of the tubes to loosen the SVF pellet, and add 10 ml of ACK lysis buffer to one tube using a 10 ml pipet. |
| 17 | Using the same pipet, re-suspend the pellet by gentle trituration, then transfer the suspension to recover the second pellet and transfer to the labeled 15 ml centrifuge tube. Place the tube in the 15 ml tube bucket and balance the rotor. Centrifuge at 1,200 rpm for 10 minutes. |
| 18 | Aspirate the supernatant, re-cap the tube, flick the bottom of the tube to loosen the SVF pellet, and add 10 ml of HBSS using a 10 ml pipet. Triturate to produce a homogeneous suspension, remove a 25 μl sample using a sterile tip on a P20 Pipetman and add to a 0.65 mL microcentrifuge tube containing 25 μL of AO-PI Live-Dead stain. Set the centrifuge to 10° C., then place the tube in the bucket opposite a balance tube, but do not start the centrifuge |
| 19 | Load a Cellometer slide with 20 μL of the cell suspension/AO-PI mixture. Insert the Cellometer slide into the instrument and determine the cell concentration and percent viability. Save the data files, then calculate the total viable cell yield and enter all data into designated form. |
| 20 | If the Cellometer count is valid, go to step 24. If the Cellometer count is not valid, go to step 21. |
| 21 | If the Cellometer count is not valid (i.e., if the count is <1.5 × $10^5$ cells/ml), centrifuge at 1,200 rpm for 10 minutes. Remove the tube(s) from the centrifuge bucket, taking care not to disturb the SVF pellet, and place in the biosafety cabinet. Using a 10 ml pipet, carefully remove the supernatant and transfer to the clean labeled tube. Inoculate about 4 mL of this into one Bact/Alert-iAST sample bottle and about 4 mL into one Bact/Alert-iNST for process sterility testing. Then flick the bottom of the tube to loosen the SVF pellet, add 5 ml of HBSS using a 10 ml pipet and triturate to re-suspend the cells. Remove a 25 μl sample using a sterile tip on a P200 Pipetman and place in 25 μL of AO-PI, then load a Cellometer slide and recount. If the count is still less than 1.5 × $10^5$ vc/mL, the yield is inadequate for cryopreservation of a client sample. |
| 22 | If the re-count is valid, place the tube(s) in the 15 ml tube bucket and balance the rotor. Set the centrifuge to 10° C., then place the tube in the bucket opposite a balance tube and centrifuge at 1,200 rpm for 10 minutes. |
| 23 | Remove the tube(s) from the centrifuge bucket, taking care not to disturb the SVF pellet, and place in the biosafety cabinet. |

It will be appreciated by those skilled in the an that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method of isolation of stromal vascular derived stem cells comprising the steps of:

a. supplying a shipment package comprising a defined client sample container having a first filter and a second filter;

b. inspecting the shipment package components for (i) integrity of the client sample container containing an adipose tissue sample and collection medium and (ii) completed recording information, contained therein;

c. introducing the shipment package components to a processing module of a database via a log-in port by scanning a barcode on the client sample container in the completed recording information;

d. testing the sterility of the adipose tissue sample from the client sample container;
e. removing the remaining collection medium in the client sample container;
f. washing the adipose tissue sample;
g. preparing a digestion solution by diluting an enzyme stock solution based on the amount of enzyme activity;
h. injecting the digestion solution into the sample container containing the adipose tissue sample to form a digestion mixture within the client sample container;
i. incubating the digestion mixture;
j. centrifuging the incubated digestion mixture;
k. withdrawing a stromal vascular fraction phase of the centrifuged digestion mixture, wherein the stromal vascular fraction consists of the fluid phase below the floating mature adipocytes and oil from lysed adipocytes;
l. centrifuging a suspension of the digestion mixture in order to isolate a first stromal vascular pellet from the digestion solution;
m. removing supernatant of the centrifuged suspension isolated in l;
n. re-suspending the first stromal vascular pellet by trituration in red blood cell lysis buffer forming a cell suspension;
o. centrifuging the cell suspension to form a second pellet;
p. removing supernatant of the centrifuged solution isolated in o;
q. re-suspending the second pellet by trituration adding salt solution forming a second suspension;
r. centrifuging the second cell suspension to form a third pellet comprising a mixture of cells of pre-adipocytes, adipose-derived mesenchymal stem cells, microvascular endothelial cells, endothelial progenitor cells, and monocytes; wherein the mixture of cells either i) does not contain mature adipocytes, and demonstrates a combined viability by acridine orange/propidium iodide or trypan blue dye-exclusion assay of no less than 35%, or ii) at least 1% of the nucleated cells in the mixture are adipose-derived mesenchymal stem cells; and
s. retaining the supernatant from the third pellet for a secondary sterility test sample;
wherein the sample container comprises three female ports disposed on a top portion of the sample container and one three-way port disposed at a bottom of a tapered section of the sample container, the three-way port including a spike port positioned perpendicular to a bottom side of the sample container, and where each of the ports comprises a removable cap,
wherein the first filter is position between the top portion and the tapered bottom of the sample container and the second filter is in the center of the tapered bottom proximal to the port located in the center of the tapered bottom,
wherein the method further comprises filtering the digestion mixture via the first filter to allow individual cells of the stromal vascular fraction phase to pass through but excluding large mature adipocytes and smaller cells held together by cellular matrix, wherein the filtering of the digestion mixture initiates at step h. and terminates at step j.,
wherein the method further comprises filtering the digestion mixture via the second filter immature adipocytes and small clumps of cells while allowing the isolated first stromal vascular fraction phase cells such as adipose stromal cells and endothelial progenitor cells to pass through the second filter, wherein the filtering of the digestion mixture initiates at step h. and terminates at step j.

2. The method of claim 1, wherein inspecting the shipment package comprises: ensuring that (a) the sample container is not past a defined expiration date, (b) the adipose tissue sample was collected within the past 36 hours, and (c) the recording information is accurate.

3. The method of claim 2, wherein the method further comprises testing the sterility of the adipose tissue sample after step b.

4. The method of claim 3, wherein preparing a digestion solution comprises the steps of: combining collagenase, neutral protease, and DNase I with a salt solution pre-warmed to 37° C.

5. The method of claim 4, wherein the method further comprises removing a sample of the re-suspended sample of step m. and calculating the total viable cell yield and recording results of the total viable cell yield.

6. The method of claim 5, wherein the method further comprises testing sterility of the supernatant obtained in step p.

7. The method of claim 6, wherein the sample container has at least one port on an upper portion of the sample container and at least one port on a lower portion of the sample container.

8. The method of claim 7, wherein the sample container is made of a material which does not release or leach any potentially toxic substance into stored cells.

9. The method of claim 8, wherein the sample container is made of a material selected from the group consisting of ethyl vinyl acetate, polyethylene, fluoro ethylene propylene and combinations thereof.

10. The method of claim 9, wherein the sample container is sterile and approximately 100 ml to 200 ml in volume.

* * * * *